US012765759B2

(12) United States Patent
Watanabe et al.

(10) Patent No.: US 12,765,759 B2
(45) Date of Patent: Oct. 20, 2026

(54) ENDOSCOPE AND ENDOSCOPIC DEVICE

(71) Applicant: HOYA CORPORATION, Tokyo (JP)

(72) Inventors: Toshiki Watanabe, Tokyo (JP); Yoshiyuki Niijima, Tokyo (JP)

(73) Assignee: PENTAX MEDICAL CORPORATION, Tokyo (JP)

( * ) Notice: Subject to any disclaimer, the term of this patent is extended or adjusted under 35 U.S.C. 154(b) by 853 days.

(21) Appl. No.: 17/615,728

(22) PCT Filed: Sep. 25, 2020

(86) PCT No.: PCT/JP2020/036292
§ 371 (c)(1),
(2) Date: Dec. 1, 2021

(87) PCT Pub. No.: WO2021/070634
PCT Pub. Date: Apr. 15, 2021

(65) Prior Publication Data

US 2022/0240768 A1 Aug. 4, 2022

(30) Foreign Application Priority Data

Oct. 8, 2019 (JP) ................................ 2019-185359

(51) Int. Cl.
*A61B 1/06* (2006.01)
*A61B 1/00* (2006.01)
(Continued)

(52) U.S. Cl.
CPC .......... *A61B 1/0669* (2013.01); *A61B 1/0005* (2013.01); *A61B 1/05* (2013.01);
(Continued)

(58) Field of Classification Search
CPC ....... A61B 1/0669; A61B 1/0005; A61B 1/05; A61B 1/0607; A61B 1/0625; A61B 1/07;
(Continued)

(56) References Cited

U.S. PATENT DOCUMENTS 8,764,644 B2 7/2014 Kuroda
2007/0118013 A1* 5/2007 Miyagi .................... A61B 1/07 600/176
(Continued)

FOREIGN PATENT DOCUMENTS

CN 102440750 5/2012
JP 05-297288 11/1993
(Continued)

OTHER PUBLICATIONS

Apr. 28, 2023 Chinese Office Action in corresponding Chinese Application No. 202080032595.2.
(Continued)

*Primary Examiner* — Michael J Carey
*Assistant Examiner* — Christen A. Sharpless
(74) *Attorney, Agent, or Firm* — GREENBLUM & BERNSTEIN, P.L.C.

(57) ABSTRACT

An endoscope includes: an imaging unit that is incorporated in a distal tip of an insertion tube and images an observed site through an observation window; a plurality of first LEDs juxtaposed outside the imaging unit; and a plurality of second LEDs juxtaposed outside a region where the first LEDs are juxtaposed. The region where the first LEDs are juxtaposed and a region where the second LEDs are juxtaposed are covered with a light distribution lens, light emission of the first LED is output to an angular range smaller than a viewing angle of the imaging unit through the light distribution lens, and light emission of the second LED is output to an angular range smaller than the viewing angle of the imaging unit through the light distribution lens.

18 Claims, 10 Drawing Sheets

(51) Int. Cl.
*A61B 1/05* (2006.01)
*A61B 1/07* (2006.01)

(52) U.S. Cl.
CPC .......... *A61B 1/0607* (2013.01); *A61B 1/0625* (2022.02); *A61B 1/07* (2013.01)

(58) Field of Classification Search
CPC . A61B 1/00096; A61B 1/0623; A61B 1/0638; A61B 1/0655; A61B 1/0684; A61B 1/0676; A61B 1/04; A61B 1/0646; A61B 1/0661; G02B 23/26
See application file for complete search history.

(56) References Cited

U.S. PATENT DOCUMENTS

| | | | | |
|---|---|---|---|---|
| 2009/0131931 | A1* | 5/2009 | Lee | A61B 5/0084 606/41 |
| 2009/0231418 | A1 | 9/2009 | Higuchi | |
| 2012/0083656 | A1* | 4/2012 | Kuroda | A61B 1/063 600/165 |
| 2014/0194686 | A1 | 7/2014 | Murayama | |
| 2016/0103312 | A1* | 4/2016 | Furuta | A61B 1/0607 362/558 |
| 2017/0290498 | A1* | 10/2017 | Tamura | F21V 9/45 |
| 2018/0098686 | A1* | 4/2018 | Tamiya | A61B 1/0008 |
| 2018/0218508 | A1* | 8/2018 | Lee | G06T 7/174 |

FOREIGN PATENT DOCUMENTS

| | | |
|---|---|---|
| JP | 2001-258823 | 9/2001 |
| JP | 2001258823 A * | 9/2001 |
| JP | 2004-321244 | 11/2004 |
| JP | 2005-073708 | 3/2005 |
| JP | 2006-34543 | 2/2006 |
| JP | 2009-219573 | 10/2009 |
| JP | 2011-024901 | 2/2011 |
| JP | 2012-75562 | 4/2012 |
| JP | 2015-16021 | 1/2015 |
| JP | 2016-128024 | 7/2016 |
| JP | 2016-202441 | 12/2016 |
| JP | 2019-130049 | 8/2019 |
| WO | 2016/203626 | 12/2016 |

OTHER PUBLICATIONS

International Search Report issued in International Bureau of WIPO Patent Application No. PCT/JP2020/036292, dated Nov. 24, 2020, along with an English translation thereof.

* cited by examiner

A

B

ENDOSCOPE AND ENDOSCOPIC DEVICE

TECHNICAL FIELD

The present invention relates to an endoscope and an endoscope device.

BACKGROUND ART

An endoscope is a medical instrument that enables observation and treatment of a desired site by being inserted into a body cavity of a subject, and includes an imaging unit incorporated in a distal tip of an insertion tube inserted into the body cavity, and an illumination device that illuminates an imaging field of view of the imaging unit. Patent Literature 1 discloses an endoscope that includes an illumination device realizing illumination in a wide angular range of 180° or more and enables observation at a wide viewing angle.

In recent years, endoscopes capable of performing image-enhanced observation obtained under illumination with narrow-band light (purple light, green light, and the like) in addition to observation under white light have been also widely used, and Patent Literature 2 discloses an endoscope device that acquires an image by alternately emitting white light and narrow-band light.

CITATION LIST

Patent Literature

Patent Literature 1: JP 2015-16021 A
Patent Literature 2: JP 2016-128024 A

SUMMARY OF INVENTION

Technical Problem

Observation under illumination with white light and narrow-band light disclosed in Patent Literature 2 is also possible in the endoscope having the wide viewing angle disclosed in Patent Literature 1. However, a spectrum of the narrow-band light is limited, and it is difficult to secure a required light amount to the entire field of view under the same condition as the white light.

An object of the present disclosure is to provide an endoscope and an endoscope device capable of satisfactorily observing a wide viewing angle under illumination with white light and narrow-band light.

Solution to Problem

An endoscope according to the present disclosure includes: an imaging unit that is incorporated in a distal tip of an insertion tube and images an observed site through an observation window; a first light output unit that is disposed around the observation window and outputs first illumination light for illuminating the observed site; and a second light output unit that is disposed around the observation window and outputs second illumination light for illuminating the observed site with an angular range larger than an angular range of the first light output unit.

The endoscope further includes: a plurality of first light emitting elements juxtaposed outside the imaging unit; a plurality of second light emitting elements juxtaposed outside a region where the first light emitting elements are juxtaposed; and a light distribution lens that is disposed around the observation window and covers the region where the first light emitting element are juxtaposed and a region where the second light emitting element are juxtaposed. The first light output unit includes the first light emitting elements and the light distribution lens, and the second light output unit includes the second light emitting elements and the light distribution lens.

Alternatively, the endoscope further includes: a light guide fiber that has a plurality of exit ends juxtaposed outside the imaging unit; a light source that emits light to be incident on an incident end of the light guide fiber; a plurality of light emitting elements juxtaposed outside a region where the exit ends are juxtaposed; and a light distribution lens that is disposed around the observation window and covers the region where the exit ends are juxtaposed and a region where the light emitting elements are juxtaposed. The first light output unit includes the light guide fiber, the light source, and the light distribution lens, and the second light output unit includes the light emitting elements and the light distribution lens.

Alternatively, the endoscope further includes: a light guide fiber that has an exit end outside the imaging unit; a first light source that faces an incident end of the light guide fiber and emits light to be incident on a central part of the incident end; a second light source that faces the incident end of the light guide fiber and emits light to be incident on the entire incident end; and a light distribution lens that covers the exit end of the light guide fiber. The first light output unit includes the light guide fiber, the first light source, and the light distribution lens, and the second light output unit includes the light guide fiber, the second light source, and the light distribution lens.

Further, an angular range of the second illumination light from the second light output unit is equal to or larger than a viewing angle of the imaging unit.

Further, the imaging unit has a viewing angle of 180° or more.

Further, the first illumination light is narrow-band light, and the second illumination light is white light.

An endoscope device according to the present disclosure includes: an endoscope including an imaging unit that is incorporated in a distal tip of an insertion tube and images an observed site through an observation window, a first light output unit that is disposed around the observation window and outputs first illumination light for illuminating the observed site, and a second light output unit that is disposed around the observation window and outputs second illumination light for illuminating the observed site with an angular range larger than an angular range of the first light output unit; and an image processing unit that performs mask processing on a peripheral edge portion of a captured image of the imaging unit under illumination by the first light output unit or the second light output unit and outputs the processed image.

Further, a captured image under illumination by the first light output unit or a captured image under illumination by the second light output unit are alternately acquired and displayed side by side.

Advantageous Effects of Invention

According to the present disclosure, it is possible to observe the wide viewing angle under the illumination with white light and narrow-band light.

DESCRIPTION OF EMBODIMENTS

Hereinafter, embodiments of the present disclosure will be described with reference to the drawings.

First Embodiment

Figure 1:
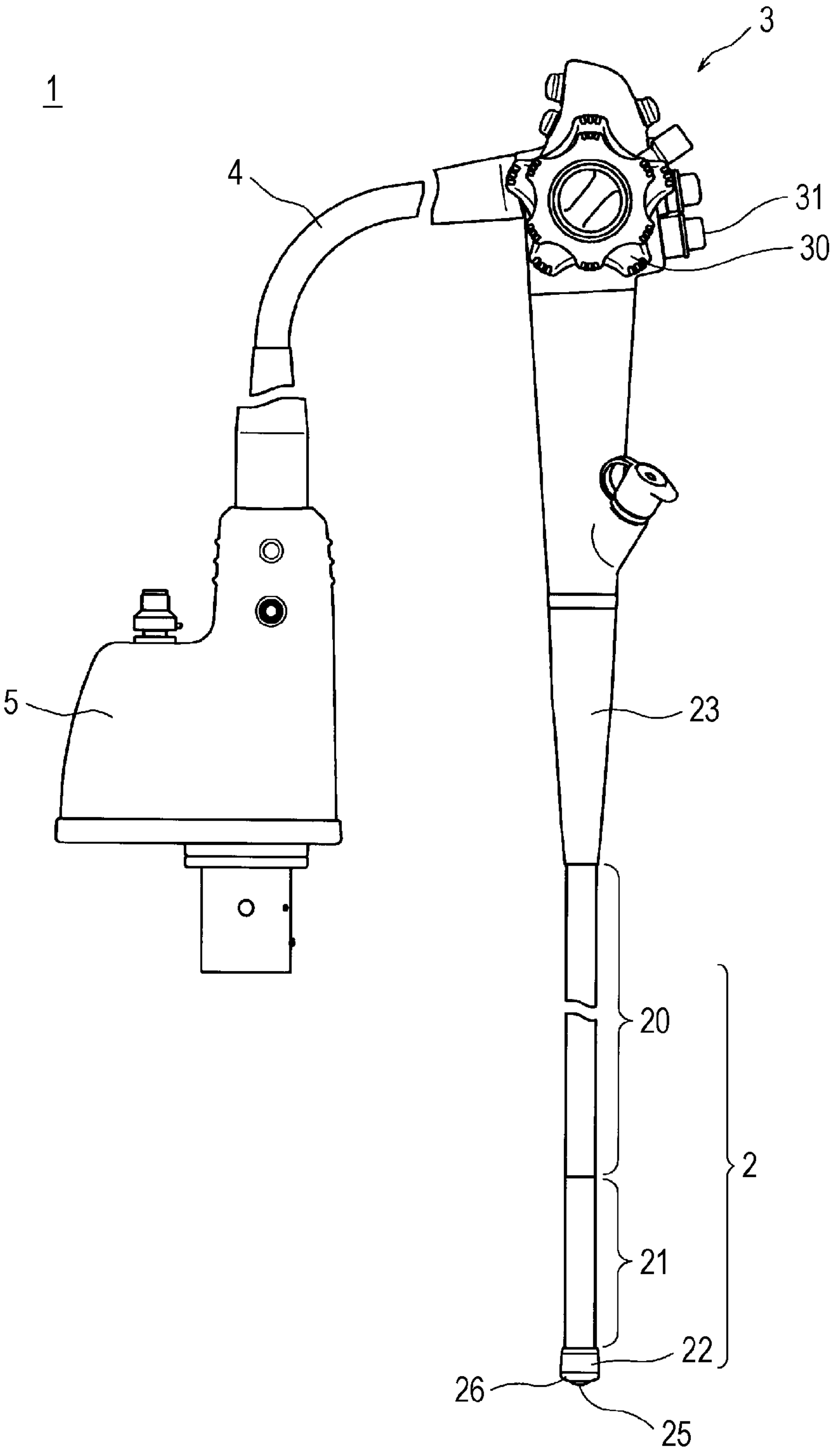
FIG. 1 is an exterior view of an endoscope.

FIG. 1 is an exterior view of an endoscope. As illustrated in the drawing, an endoscope 1 includes an insertion tube 2, an operation unit 3, a universal tube 4, and a connector unit 5. The insertion tube 2 is a portion to be inserted into a body cavity, and includes a long soft portion 20 and a distal tip 22 connected to one end of the soft portion 20 via a bending section 21. The other end of the soft portion 20 is connected to an operation unit 3 via a cylindrical connecting portion 23. One end of the universal tube 4 is connected to the operation unit 3 and extends in a direction different from the insertion tube 2, and the connector unit 5 is connected to the other end of the universal tube 4.

The operation unit 3 is provided to be gripped by a user to perform various operations, and includes a bending operation knob 30, a plurality of operation buttons 31, and the like. The bending operation knob 30 is connected to the bending section 21 by a wire (not illustrated) passing through the inside of each of the connecting portion 23 and the soft portion 20. The bending section 21 is bent in two directions orthogonal to each other in an axial section by the operation of the bending operation knob 30, thereby changing a direction of the distal tip 22 inserted into the body cavity.

Figure 2:
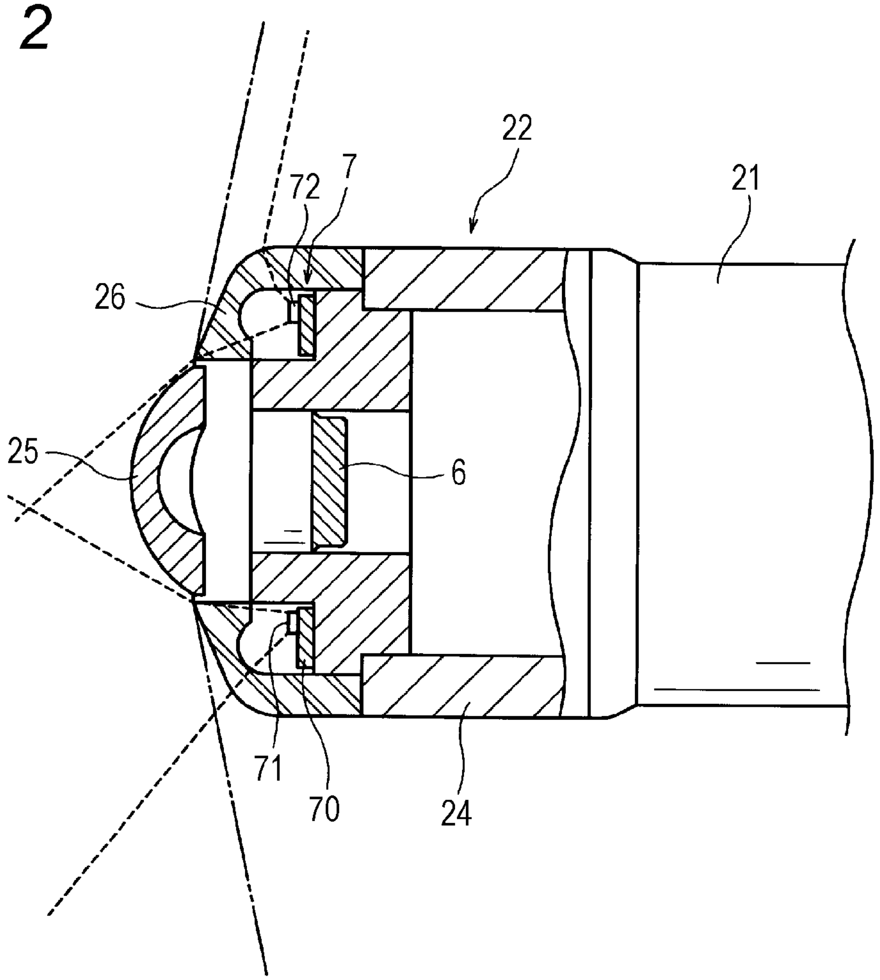
FIG. 2 is an enlarged view of a distal tip of an insertion tube.

FIG. 2 is an enlarged view of the distal tip 22 of the insertion tube 2, and illustrates a main portion in a broken manner. The distal tip 22 includes a cylindrical housing 24 whose one side is fixed to the bending section 21. The other side of the housing 24 is covered with a central observation window 25 and an annular light distribution lens 26 surrounding the periphery of the observation window 25. In the housing 24, an imaging unit 6 is incorporated to face the inside of the observation window 25, and an illumination unit 7 is incorporated to face the inside of the light distribution lens 26.

The imaging unit 6 includes an image sensor such as a complementary metal oxide semiconductor (CMOS) and an optical system configured to form an image on an imaging surface of the image sensor, and images the inside of the body cavity through the observation window 25. The observation window 25 is a wide-angle objective lens, and the imaging unit 6 is configured to be capable of imaging at a viewing angle of 180° or more by setting of the optical system including the observation window 25. A two-dot chain line in FIG. 2 indicates an imaging field of view of the imaging unit 6.

Figure 3:
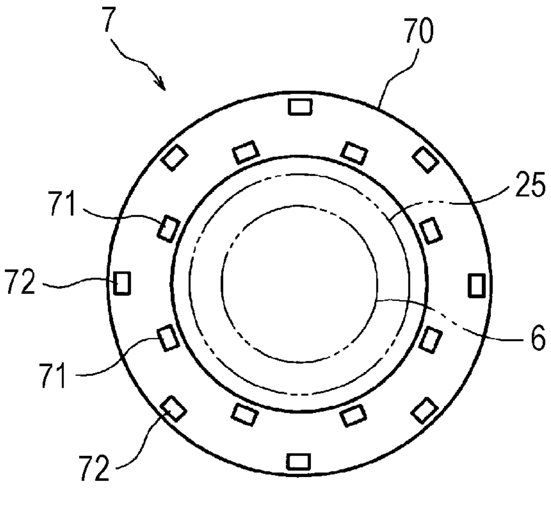
FIG. 3 is a plan view illustrating an arrangement example of a first LED and a second LED.

The illumination unit 7 includes an annular substrate 70 surrounding the periphery of the imaging unit 6, and first LEDs 71 and second LEDs 72 mounted on one surface of the substrate 70 facing the light distribution lens 26. FIG. 3 is a plan view illustrating an arrangement example of the first LED 71 and the second LED 72. A plurality of (eight in the drawing) first LEDs 71 and a plurality of (eight in the drawing) second LEDs 72 are provided, the first LEDs 71 are arranged at substantially equal intervals on an inner peripheral side (the side close to the imaging unit 6) of the annular substrate 70, and the second LEDs 72 are arranged at substantially equal intervals outside an arrangement region of the first LEDs 71. In FIG. 3, positions of the imaging unit 6 and the observation window 25 are indicated by two-dot chain lines.

The lower half of FIG. 2 illustrates a cross section at an arrangement position of the first LED 71, and the upper half of FIG. 2 illustrates a cross section at an arrangement position of the second LED 72. The light distribution lens 26 is a cylindrical lens having a shape that extends outward from a peripheral edge portion of the observation window 25 and is continuous to a peripheral wall of the housing 24 through a bending portion, and light emitted from the first LED 71 or the second LED 72 is emitted through the light distribution lens 26 and illuminates an imaging field of view of the imaging unit 6.

Broken lines in FIG. 2 indicate light distribution ranges of the first LED 71 and the second LED 72. The light emitted from the first LED 71 located inside is incident on a spread portion of the light distribution lens 26, and is intensively distributed to a central portion of the imaging field of view of the imaging unit 6. On the other hand, the light emitted from the second LED 72 located outside is incident on a wide range from the spread portion to the bending portion of the light distribution lens 26 to greatly spreads, and is distributed to the entire imaging field of view of the imaging unit 6. Note that a concave portion is provided in the vicinity of the bending portion on an inner surface of the light distribution lens 26. The light distribution of the second LED 72 becomes wider than the light distribution of the first LED 71 by the action of the concave portion. In other words, a light irradiation range by the second LED 72 is wider than a light irradiation range by the first LED 71.

The first LED 71 emits narrow-band light including wavelength ranges of violet and green. For example, every other four of the eight first LEDs 71 are green LED chips that emit green light, the remaining four are violet LED chips that emit ultraviolet light, and the eight first LEDs 71 and the light distribution lens 26 constitute a first light output unit that outputs narrow-band light.

The second LED 72 is a white LED that emits white light, and is configured by, for example, covering a light emitting surface of a blue LED chip that emits blue light with a yellow phosphor. The second LEDs 72 and the light distribution lens 26 constitute a second light output unit that outputs white light. The first and second LEDs 71 and 72 may be other light emitting elements such as LDs.

Imaging by the imaging unit 6 is performed under illumination with the narrow-band light output from the first light output unit or the white light output from the second light output unit. A light distribution angle of the white light is larger than a light distribution angle of the narrow-band light, desirably is almost equal to a viewing angle of the imaging unit 6 desirably, and more desirably equal to or larger than the viewing angle of the imaging unit 6. Then, the imaging can be performed under a sufficient light amount in the entire field of view. Although a spectrum of the narrow-band light is limited, the imaging can be performed under a light amount equivalent to that of the white light within the light distribution range since the light distribution angle of the narrow-band light is smaller than the light distribution angle of the white light.

Figure 4:
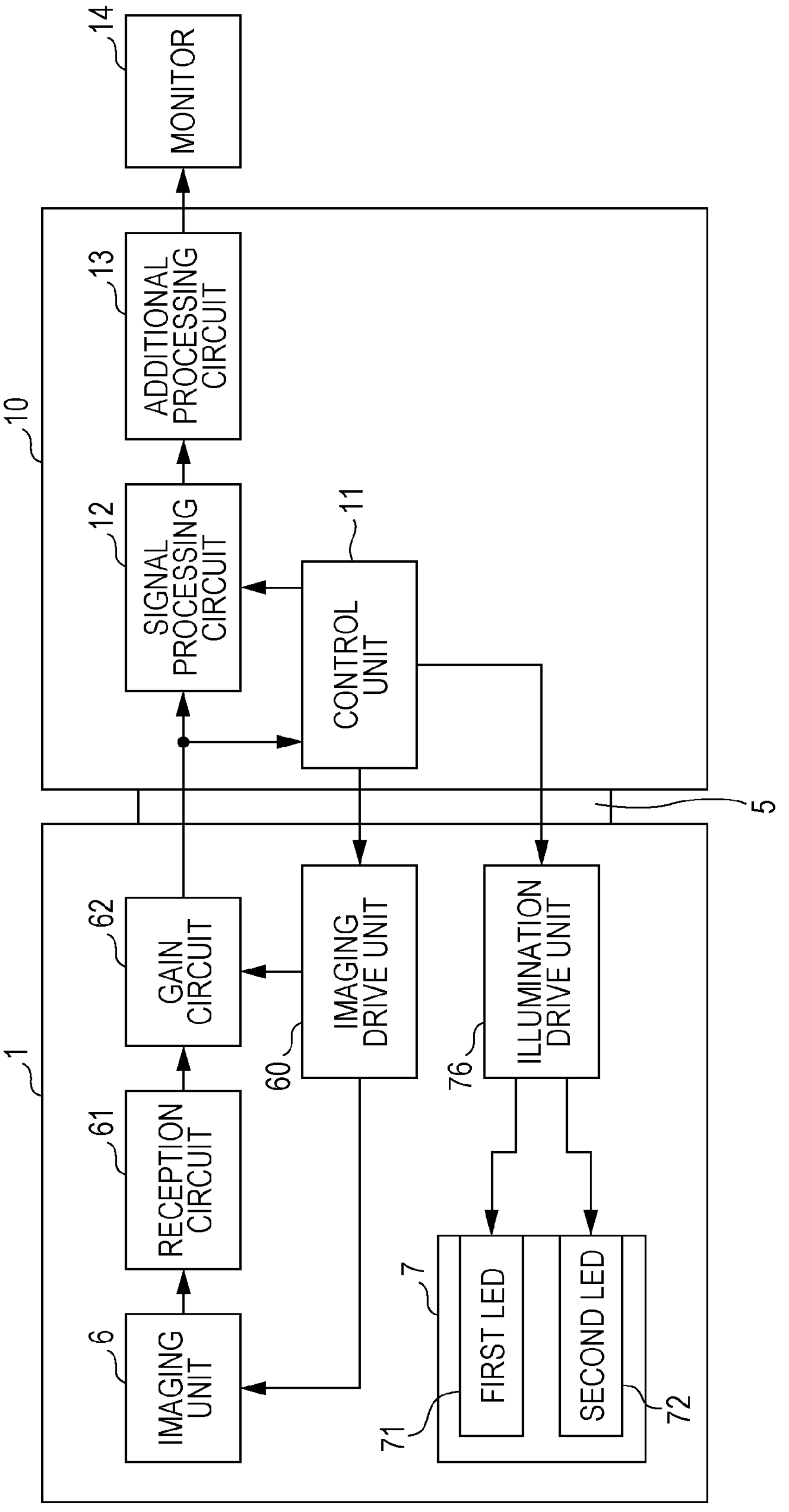
FIG. 4 is a block diagram of an endoscope device.

FIG. 4 is a block diagram of an endoscope device. The endoscope 1 is connected to a processor device 10 via the connector unit 5 and used as the endoscope device. The processor device 10 includes a control unit 11, a signal processing circuit 12, an additional processing circuit 13, and the like. The control unit 11 includes a CPU, a ROM, and a RAM, and integrally controls the endoscope device by the operation of the CPU according to a control program stored in the ROM.

The endoscope 1 includes an imaging drive unit 60 that drives the imaging unit 6 and an illumination drive unit 76 that drives the illumination unit 7. The imaging drive unit 60 drives the imaging unit 6 by a rolling shutter method according to a control command given from the control unit 11. An output signal of the imaging drive unit 60 is given to a gain circuit 62 in a unit of one frame through a reception circuit 61, and predetermined preprocessing, such as white balance processing, is performed to output an image signal to the signal processing circuit 12 of the processor device 10. For the preprocessing of the gain circuit 62, a gain value given from the imaging drive unit 60 is used.

The illumination drive unit 76 drives the illumination unit 7 according to a control command given from the control unit 11, and causes the first LED 71 and the second LED 72 to selectively or alternately emit light. An imaging operation of the imaging unit 6 is executed in synchronization with the driving of the illumination unit 7, and an image output obtained under illumination of the narrow-band light by the first LED 71 or under illumination of the white light by the second LED 72 is continuously or alternately input to the signal processing circuit 12. An operation mode of the illumination unit 7 can be selected by operating the operation button 31 provided on the operation unit 3.

The signal processing circuit 12 performs image processing, such as gamma correction and interpolation processing, on an input image, and outputs the processed image to the additional processing circuit 13. The additional processing circuit 13 performs mask processing on a peripheral edge portion, performs zoom processing on an image under narrow-band light, further converts the image into an image conforming to a predetermined standard by superimposition processing of various characters and images, and outputs the converted image to an external monitor 14. Note that a region to be subjected to the mask processing may be expanded without performing the zoom processing in the image under the narrow-band light. The monitor 14 is a display device such as a liquid crystal display and an organic EL display, and displays a captured image of the imaging unit 6 based on an image signal output from the processor device 10. The user of the endoscope 1 can observe a desired site in the body cavity under the illumination of narrow-band light or white light through the display of the monitor 14.

Figure 5:
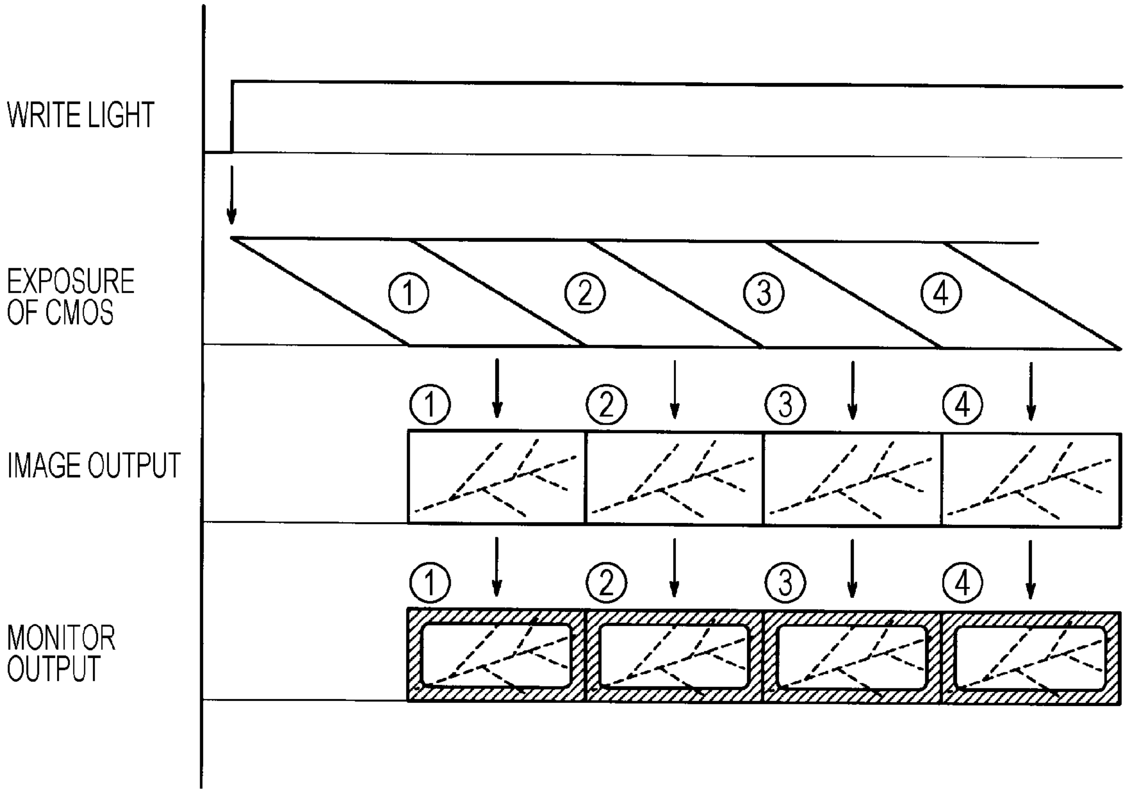
FIG. 5 is an explanatory view illustrating a flow of an imaging process.
Figure 6:
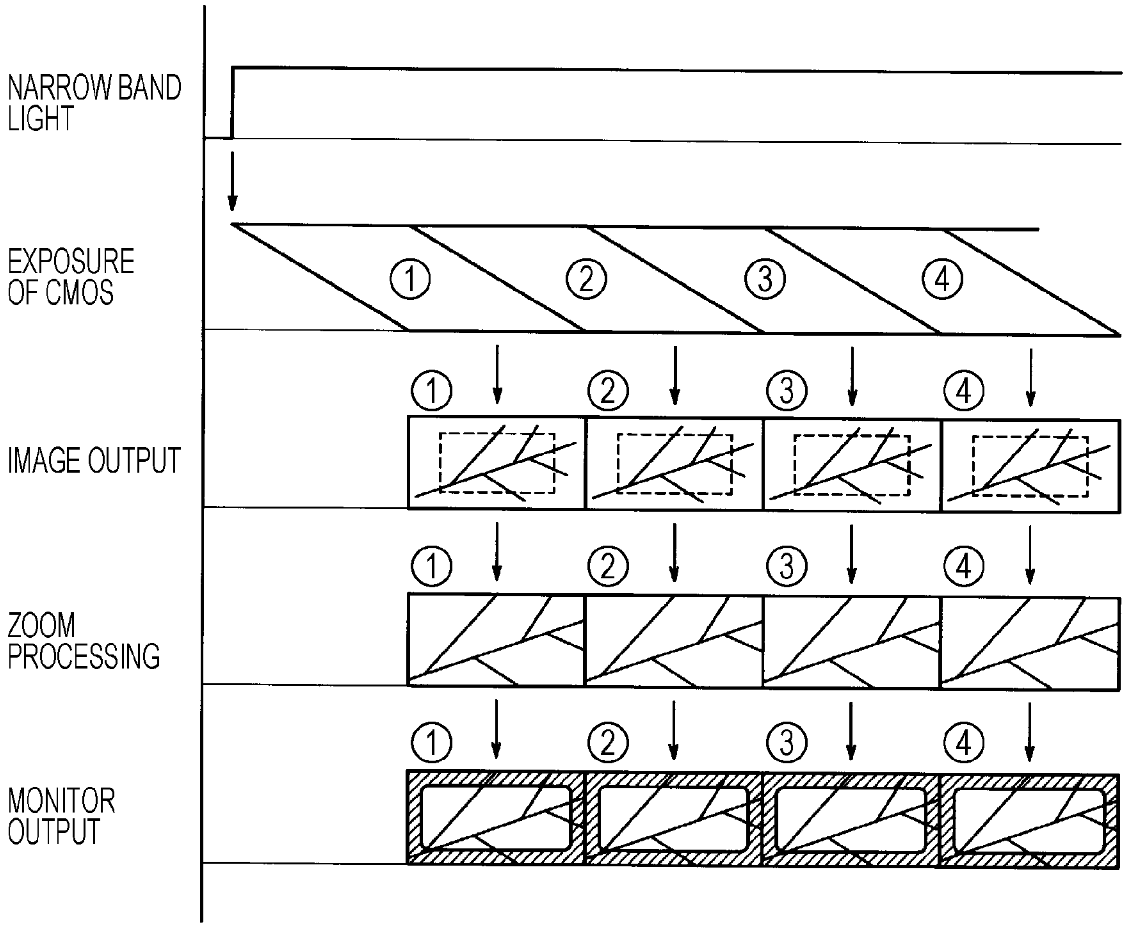
FIG. 6 is an explanatory view illustrating a flow of an imaging process.
Figure 7:
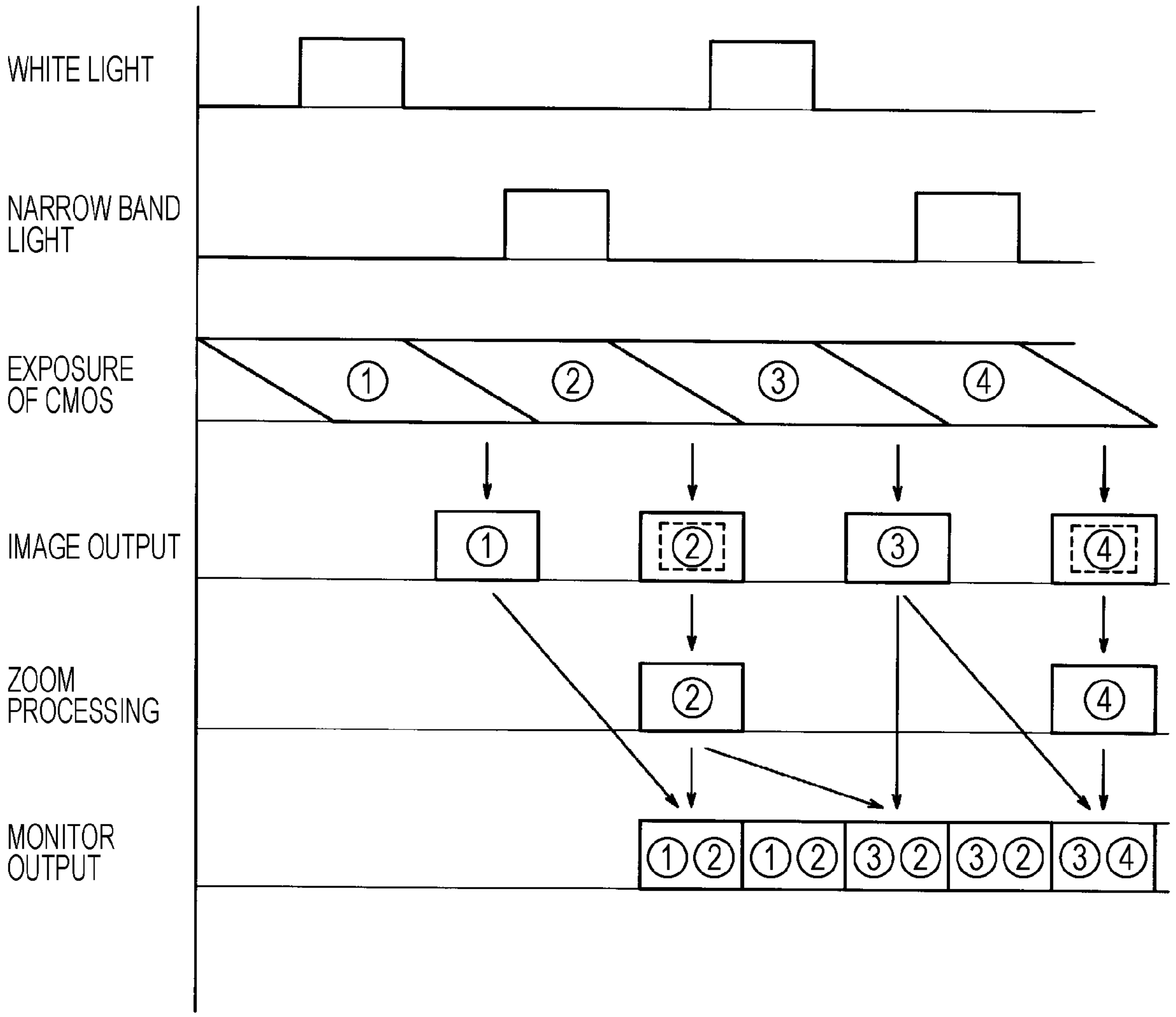
FIG. 7 is an explanatory view illustrating a flow of an imaging process.

FIGS. 5 to 7 are explanatory views illustrating flows of imaging processing. FIG. 5 illustrates a flow in an environment of single illumination with white light, FIG. 6 illustrates a flow in an environment of single illumination with narrow-band light, and FIG. 7 illustrates a flow in an environment of alternate illumination with white light and narrow-band light.

As illustrated in FIGS. 5 and 6, an image output is given to the processor device 10 in a unit of one frame by the exposure of the CMOS of the imaging unit 6 and is output to the monitor 14 through the above-described processing, under the single illumination of the white light or the narrow-band light. Since the angular range larger than the viewing angle of the imaging unit 6 is illuminated by the white light, an image with a sufficient light amount over the entire surface is obtained under the white light, and this image is displayed on the monitor 14 as an image of which a peripheral edge portion (black portion) has been masked by the mask processing.

On the other hand, an illumination range of the narrow-band light is smaller than the viewing angle of the imaging unit 6, and thus, an image output under the narrow-band light is displayed on the monitor 14 as an image of which a central portion surrounded by broken lines is enlarged by the zoom processing and a peripheral edge portion (black portion) is masked by the mask processing. Note that, in a case where the imaging unit 6 has an optical zoom function, the zoom processing can be omitted by utilizing this function.

The narrow-band light is light including a violet or green wavelength region, and an image in which capillaries and microstructural patterns of a tissue surface layer in a body cavity are emphasized is obtained under the narrow-band light. In FIG. 6, capillaries indicated by broken lines in FIG. 5 are indicated by solid lines. The narrow-band light is not limited to light including the violet or green wavelength region, and may be light of another wavelength region, or a combination of light of a plurality of kinds of wavelength regions.

For example, the user of the endoscope 1 can roughly observe the inside of the body cavity by a wide-angle display image under white light, and switch the display image to a display image under narrow-band light at a desired site such as a lesion, thereby performing detailed observation. As described above, the switching of the display image can be realized by selecting the operation mode of the illumination unit 7 by operating the operation button 31 provided in the operation unit 3.

As illustrated in FIG. 7, the exposure time of the CMOS of the imaging unit 6 is extended to two frames, and white light and narrow-band light are alternately emitted for one frame length within the exposure time, in the environment of alternate illumination with the white light and narrow-band light. As a result, an image output under the white light and an image output under the narrow-band light are alternately obtained. The former is sequentially output to the monitor through the mask processing, and the latter is sequentially output to the monitor 14 through the zoom processing and the mask processing. On the monitor 14, the images under the white light and the images under the narrow-band light are displayed side by side in the individual output order.

The user of the endoscope 1 can observe the captured image under the white light and the captured image under the narrow-band light together. The alternate illumination of the white light and the narrow-band light can be realized by selecting the operation mode of the illumination unit 7 by operating the operation button 31 provided in the operation unit 3.

Second Embodiment

Figure 8:
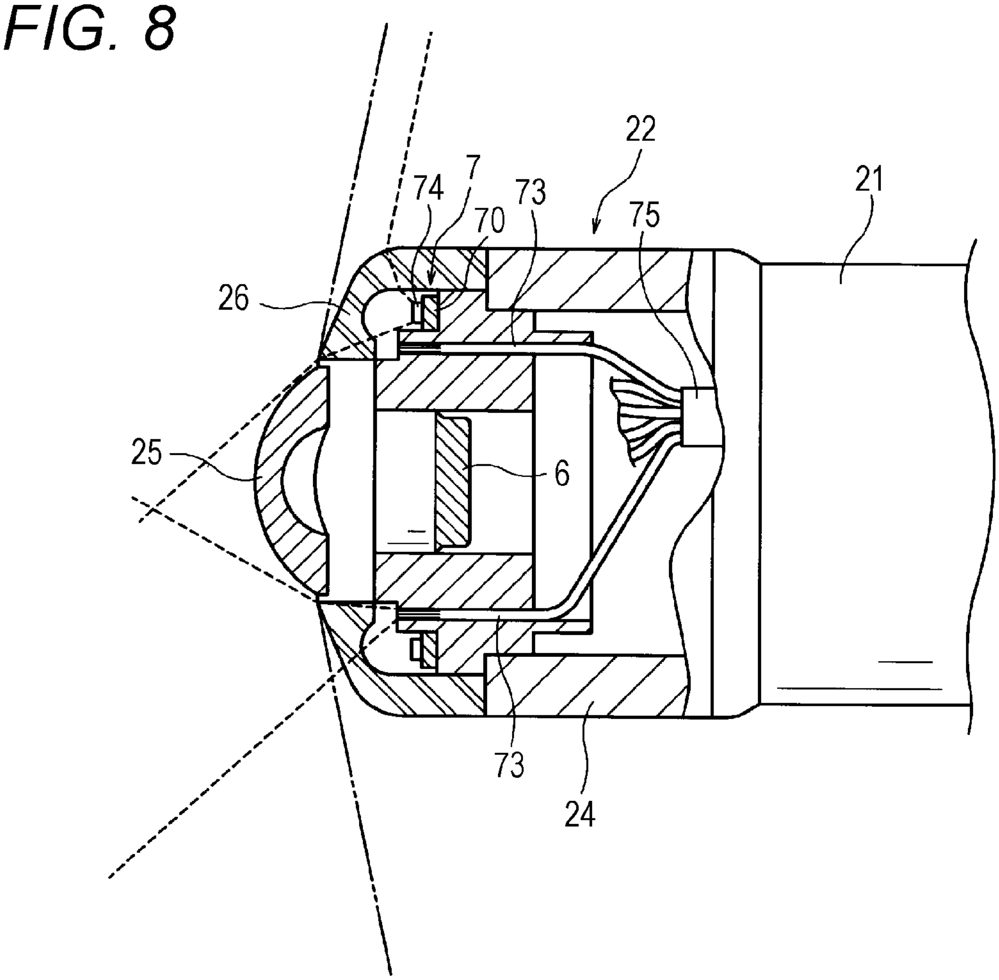
FIG. 8 is an enlarged view of a distal tip of an insertion tube of an endoscope according to a second embodiment.

FIG. 8 is an enlarged view of a distal tip of an insertion tube of an endoscope according to a second embodiment, and corresponds to FIG. 2 in the first embodiment. The second embodiment is similar to the first embodiment except for a configuration of the illumination unit 7, and corresponding components will be denoted by the same reference signs as those in FIG. 2, and the description thereof will be omitted.

Figure 9:
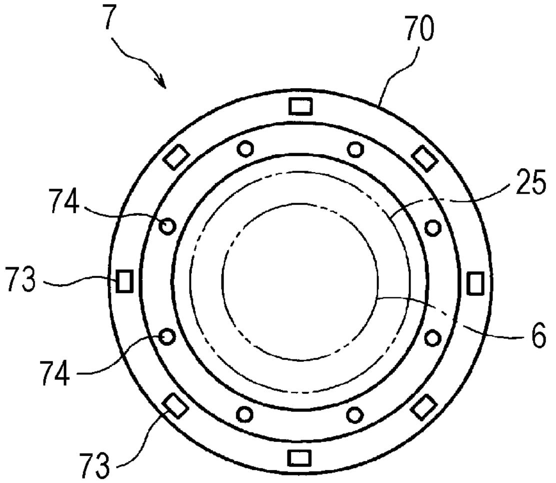
FIG. 9 is a plan view illustrating an arrangement example of an optical fiber bundle and an LED.

The illumination unit 7 faces the inside of the light distribution lens 26 and is incorporated in the housing 24, and includes optical fiber bundles 73 and LEDs 74 arranged to surround the periphery of the imaging unit 6. FIG. 9 is a plan view illustrating an arrangement example of the optical fiber bundle 73 and the LED 74. In FIG. 9, the imaging unit 6 and the observation window 25 are indicated by two-dot chain lines. The optical fiber bundles 73 have their tips (exit ends) facing the inside of the light distribution lens 26 and are juxtaposed at substantially equal intervals on a concentric circumference outside the imaging unit 6. The LEDs 74 are mounted on the annular substrate 70 arranged outside a region where the optical fiber bundles 73 are juxtaposed, and are juxtaposed at substantially equal intervals. Although each of the number of the juxtaposed optical fiber bundles 73 and the number of the juxtaposed LEDs 74 is eight in FIG. 9, the present invention is not limited thereto.

The optical fiber bundle 73 is configured by pulling out a plurality of optical fibers from a tip of a light guide fiber 75 configured by bundling a large number of optical fibers. The light guide fiber 75 extends to the connector unit 5 through the inside of the insertion tube 2, the operation unit 3, and the universal tube 4, and an end (incident end) of the light guide fiber 75 faces a light source (not illustrated) of narrow-band light inside the processor device 10. The light source can be configured by, for example, a combination of a high-luminance lamp that emits white light, such as a xenon lamp and a metal halide lamp, and a filter. Further, the light source may be a light emitting element such as an LED.

With the above configuration, the narrow-band light is emitted from the tip of the optical fiber bundle 73, is incident on a spread portion of the light distribution lens 26, and is intensively distributed to a central portion of an imaging field of view of the imaging unit 6. In the lower half part of FIG. 8, a light distribution range of the narrow-band light is indicated by a broken line.

The LEDs 74 juxtaposed outside the optical fiber bundle 73 emit white light. This emitted light is incident on a wide range from the spread portion to a bending portion of the light distribution lens 26 to greatly spreads, and is distributed to the entire imaging field of view of the imaging unit 6. In the lower half part of FIG. 8, a light distribution range of the white light is indicated by a broken line.

In the second embodiment, the optical fiber bundle 73 and the light distribution lens 26 constitute a first light output unit that outputs the narrow-band light, and the LEDs 74 and the light distribution lens 26 constitute a second light output unit that outputs the white light, so that imaging under the narrow-band light and imaging under the white light can be performed similarly to the first embodiment. Since the narrow-band light is emitted from the tip of the optical fiber bundle 73 at a small divergence angle, the light distribution range of the narrow-band light passing through the light distribution lens 26 is smaller than that in the first embodiment, and a sufficient light amount can be secured within the light distribution range. Note that the LED 74 may be another light emitting element such as an LD.

Third Embodiment

Figure 10:
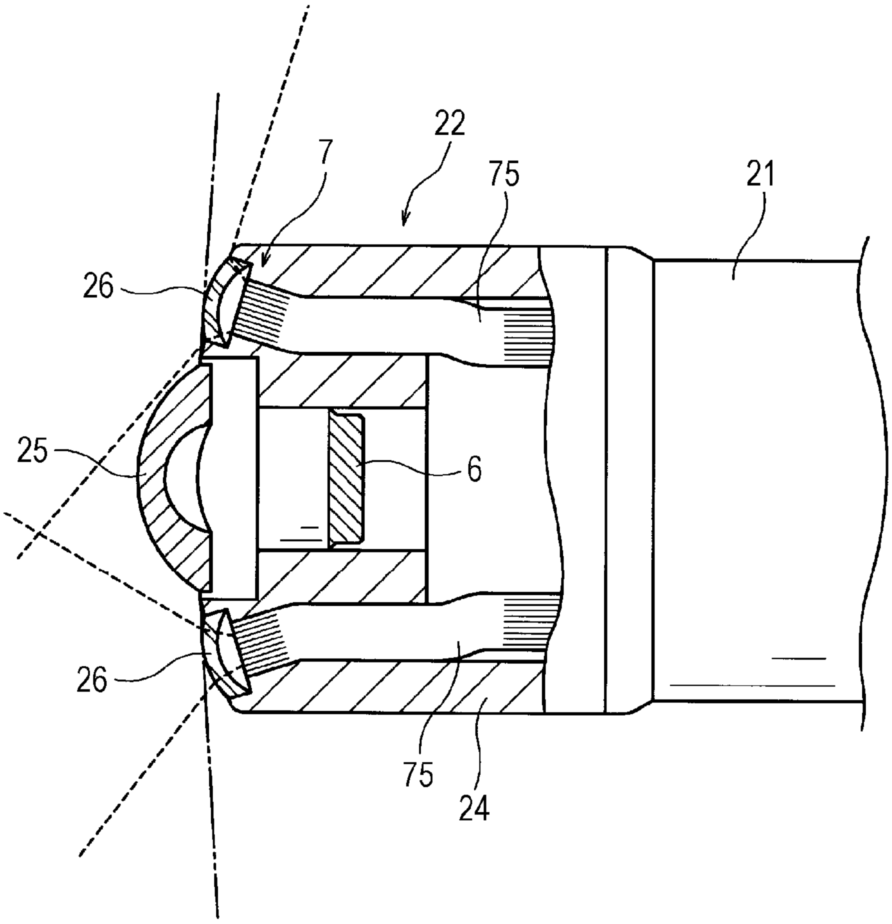
FIG. 10 is an enlarged view of a distal tip of an insertion tube of an endoscope according to a third embodiment.

FIG. 10 is an enlarged view of a distal tip of an insertion tube of an endoscope according to a third embodiment, and corresponds to FIG. 2 in the first embodiment and FIG. 8 in the second embodiment.

In the third embodiment, the observation window 25 is provided at the center on the other side of the housing 24 of the distal tip 22, and two light distribution lenses 26 and 26 are provided outside the observation window 25. The light distribution lens 26 is a concave lens having an optical axis inclined outward. The imaging unit 6 is incorporated in the housing 24 such that the imaging unit 6 faces the inside of the observation window 25, and the light guide fibers 75 constituting the illumination unit 7 are incorporated with tips (exit ends) each facing the inside of each of the light distribution lenses 26.

The light guide fiber 75 is configured by bundling a large number of optical fibers, and extends to the connector unit 5 through the inside of the insertion tube 2, the operation unit 3, and the universal tube 4, and an end (incident end) of the light guide fiber 75 faces a light source unit 8, which will be described later, inside the processor device 10 to which the connector unit 5 is connected.

Figure 11:
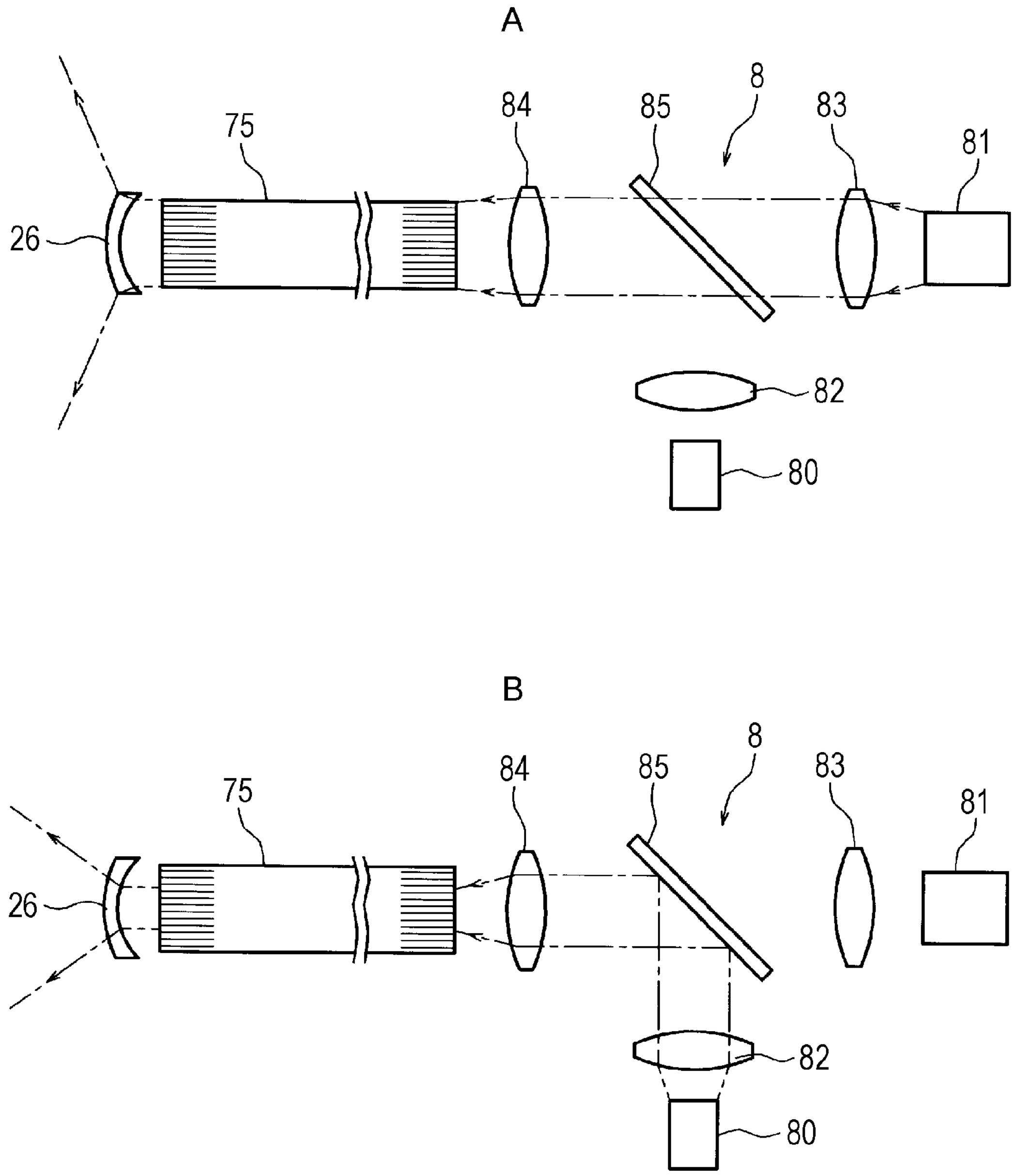
FIG. 11 is a schematic view illustrating a configuration example of a light source unit.

FIG. 11 is a schematic view illustrating a configuration example of the light source unit 8. The light source unit 8 illustrated in this drawing includes a first light source 80 and a second light source 81. The second light source 81 is a light source that emits white light, and is directly opposite to an incident end of the light guide fiber 75 on the same optical axis. A collimator lens 83, a half mirror 85, and a condenser lens 84 are arranged in this order on the optical axis between the second light source 81 and the light guide fiber 75. In FIG. 11A, an optical path of the white light emitted by the second light source 81 is indicated by a two-dot chain line. The white light becomes parallel light through the collimator lens 83, passes through the half mirror 85 to be condensed by the condenser lens 84, and is incident on the entire incident end of the light guide fiber 75.

The first light source 80 is a light source that emits narrow-band light, has an optical axis orthogonal to the second light source 81 and the light guide fiber 75, and is arranged to face the half mirror 85 via the collimator lens 82. In FIG. 11B, an optical path of the narrow-band light emitted by the first light source 80 is indicated by a two-dot chain line. The half mirror 85 has a reflecting surface that has an inclination angle of 45° with respect to the optical axis of the first light source 80, and the narrow-band light becomes parallel light through the collimator lens 82, is reflected by the half mirror 85 to reach the condenser lens 84, and is incident on the center of the incident end of the light guide fiber 75.

The incident light as described above is guided to the light guide fiber 75, reaches the exit end, and is emitted through the light distribution lens 26. Since the white light is emitted from the entire surface of the exit end, the white light is output at a large divergence angle through the light distribution lens 26. On the other hand, the narrow-band light is emitted from the center of the exit end, and thus, the narrow-band light is output at a divergence angle smaller than that of the white light. A light distribution range of the white light is indicated by a broken line in the upper half part of FIG. 10, and a light distribution range of the narrow-band light is indicated by a broken line in the lower half part of FIG. 10.

In the third embodiment, the first light source 80, the light guide fiber 75, and the light distribution lens 26 constitute a first light output unit, and the second light source 81, the light guide fiber 75, and the light distribution lens 26 constitute a second light output unit. Imaging under the narrow-band light and imaging under the white light can be performed similarly to the first and second embodiments. The first light source 80 and the second light source 81 are light emitting elements such as LEDs, or high-luminance lamps such as xenon lamps and metal halide lamps. The first light source 80 may be a combination of a plurality of types of light sources that emit light of different wavelengths. In this case, it is sufficient to arrange the half mirrors 85 corresponding to the respective light sources.

Fourth Embodiment

Figure 12:
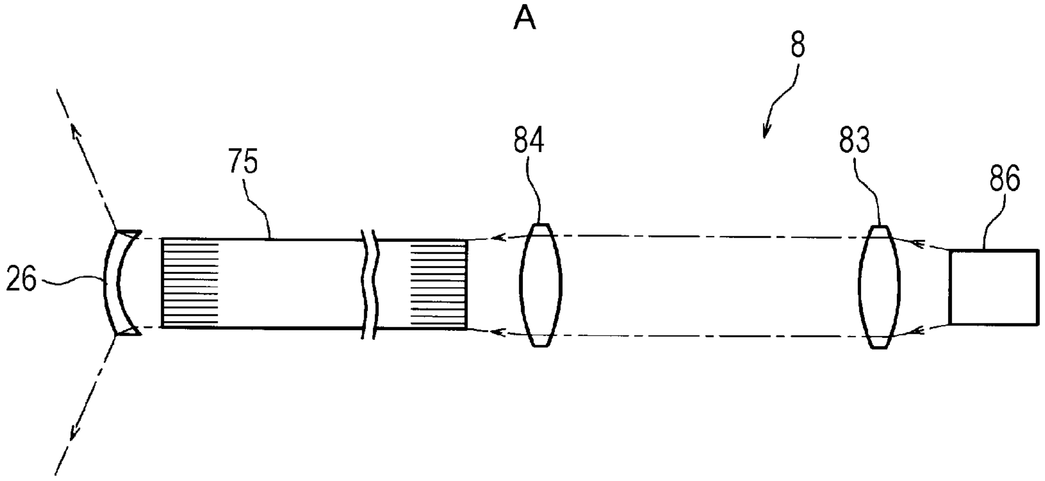
FIG. 12 is a schematic view illustrating a configuration example of a light source unit according to a fourth embodiment.
Figure 12:
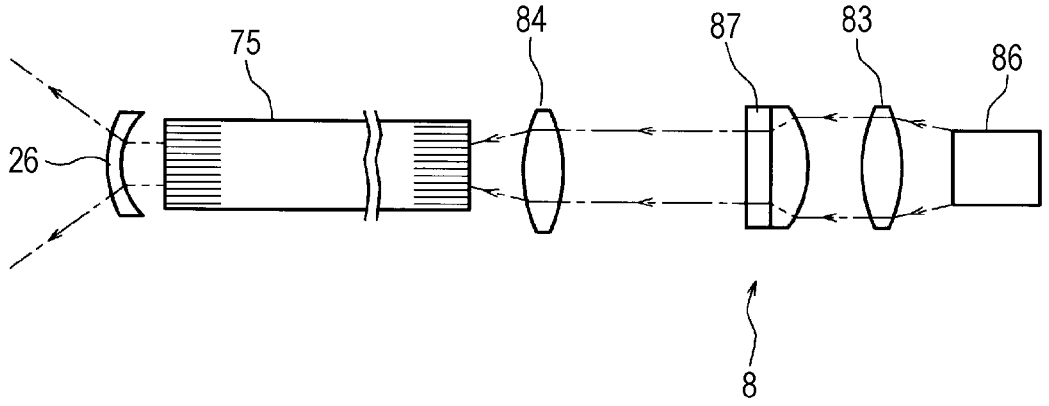

A fourth embodiment is different from the third embodiment in terms of a configuration of light source unit 8. FIG. 12 is a schematic view illustrating a configuration example of the light source unit 8 according to the fourth embodiment. The light source unit 8 illustrated in this drawing includes a single light source 86. The light source 86 faces an incident end of the light guide fiber 75 on the same optical axis and emits white light. Similarly to the third embodiment, the collimator lens 83 and the condenser lens 84 are arranged in this order on the optical axis between the light source 88 and the light guide fiber 75.

The light source unit 8 further includes a light-collecting filter 87. The light-collecting filter 87 is a combination of a filter that transmits light of a predetermined wavelength (purple light, green light, and the like) and a lens, and is arranged to be capable of being taken in and out on the optical axis between the collimator lens 83 and the condenser lens 84.

In FIG. 12A, an optical path in a case where the light-collecting filter 87 is not arranged is indicated by a two-dot chain line. In this case, the white light emitted from the light source 86 becomes parallel light through the collimator lens 83 to directly reach the condenser lens 84, and is condensed by the condenser lens 84 to be incident on the entire incident end of the light guide fiber 75.

In FIG. 12B, an optical path in a case where the light-collecting filter 87 is arranged is indicated by a two-dot chain line. In this case, the white light emitted from the light source 86 becomes parallel light through the collimator lens 83, further becomes narrow-band light in which a light flux has been narrowed through the light-collecting filter 87, reaches the condenser lens 84, and is condensed by the condenser lens 84 to be incident on the center of the incident end of the light guide fiber 75.

The incident light is guided by the light guide fiber 75, reaches an exit end, and is emitted through the light distribution lens 26, which is similar to the third embodiment. Since the white light is emitted from the entire surface of the exit end, the white light is output at a large divergence angle through the light distribution lens 26. On the other hand, the narrow-band light is emitted from the center of the exit end, and thus, the narrow-band light is output at a divergence angle smaller than that of the white light.

In the fourth embodiment, the light source 86, the light-collecting filter 87, the light guide fiber 75, and the light distribution lens 26 constitute a first light output unit, and the light source 86, the light guide fiber 75, and the light distribution lens 26 constitute a second light output unit, so that imaging under the narrow-band light and imaging under the white light can be performed similarly to the third embodiment. The light source 86 may be a high-luminance lamp, such as a xenon lamp and a metal halide lamp, or may be a light emitting element such as a white LED. The light-collecting filter 87 can be taken in and out by an appropriate actuator.

Note that the embodiments disclosed herein are exemplary in all respects, and it should be considered that the embodiments are not restrictive. The scope of the present invention is defined not by the above-described meaning but by claims, and is intended to include all modifications within significance and a scope equivalent to the claims.

REFERENCE SIGNS LIST

1 endoscope
2 insertion tube
6 imaging unit
7 illumination unit
8 light source unit
22 distal tip
25 observation window
26 light distribution lens
71 first LED (first light emitting element)
72 second LED (second light emitting element)
73 optical fiber bundle
74 LED (light emitting element)
75 light guide fiber
80 first light source
81 second light source

The invention claimed is:

1. An endoscope comprising:

an imaging unit that is incorporated in a distal tip of an insertion tube and images an observed site through an observation window;

a first light output unit that is disposed around the observation window and includes a single, annular light distribution lens that is disposed around the observation window and a first light emitting element facing the single, annular light distribution lens and positioned to emit first illumination light to pass through the single, annular light distribution lens, which transmits the first illumination light only in a first range of directions to illuminate the observed site; and a second light output unit that is disposed around the observation window includes the single, annular light distribution lens and a second light emitting element facing the single, annular light distribution lens and positioned to emit second illumination light to pass through the single, annular light distribution lens, which transmits the second illumination light only in a second range of directions different from the first range of directions of the first illumination light to illuminate the observed site, wherein the first illumination light is narrow-band light, the second illumination light is white light, and the light distribution angle of the narrow-band light emitted from the light distribution lens with respect to the optical axis of the observation window is narrower than the light distribution angle of the white light emitted from the light distribution lens.

2. The endoscope according to claim 1, further comprising:
a plurality of the first light emitting elements juxtaposed outside the imaging unit; and
a plurality of the second light emitting elements juxtaposed outside a region where the first light emitting elements are juxtaposed, wherein
the single, annular light distribution lens covers the region where the first light emitting elements are juxtaposed and a region where the second light emitting elements are juxtaposed,
the first light output unit includes the first light emitting elements and the single, annular light distribution lens, and
the second light output unit includes the second light emitting elements and the single, annular light distribution lens.

3. The endoscope according to claim 1, further comprising:
a light guide fiber that has a plurality of exit ends juxtaposed outside the imaging unit and an incident end configured to receive light emitted by the first light emitting element; and
a plurality of the second light emitting elements, wherein
the plurality of second light emitting elements are juxtaposed outside a region where the exit ends are juxtaposed,
the single, annular light distribution lens covers the region where the exit ends are juxtaposed and a region where the second light emitting elements are juxtaposed, and
the first light output unit also includes the light guide fiber, and the second light output unit includes the second light emitting elements and the single, annular light distribution lens.

4. The endoscope according to claim 1, further comprising:
a light guide fiber that has an exit end outside the imaging unit and an incident end receiving the first and second illumination light from the first and second light emitting elements, respectively, wherein
the first light emitting element emits light to be incident on a central part of the incident end,
the second light emitting element emits light to be incident on the entire incident end,
the single, annular light distribution lens covers the exit end of the light guide fiber, and
the first light output unit also includes the light guide fiber and the second light output unit also includes the light guide fiber.

5. The endoscope according to claim 1, wherein an angular range of the second illumination light from the second light output unit is equal to or larger than a viewing angle of the imaging unit.

6. The endoscope according to claim 1, wherein the imaging unit has a viewing angle of 180° or more.

7. The endoscope according to claim 1, wherein the first illumination light is narrow-band light, and the second illumination light is white light.

8. An endoscope device comprising:
an endoscope including
an imaging unit that is incorporated in a distal tip of an insertion tube and images an observed site through an observation window,
a first light output unit that is disposed around the observation window and includes a single, annular light distribution lens that is disposed around the observation window and a first light emitting element facing the single, annular light distribution lens and positioned to emit first illumination light to pass through the single, annular light distribution lens, which transmits the first illumination light only in a first range of directions to illuminate the observed site, and
a second light output unit that is disposed around the observation window and includes the single, annular light distribution lens and a second light emitting element facing the single, annular light distribution lens and positioned to emit second illumination light to pass through the single, annular light distribution lens, which transmits the second illumination light only in a second range of directions different from the first range of directions of the first illumination light to illuminate the observed site; and
an image processing unit that performs mask processing on a peripheral edge portion of a captured image of the imaging unit under illumination by the first light output unit or the second light output unit and outputs the processed image, wherein
the first illumination light is narrow-band light, the second illumination light is white light, and the light distribution angle of the narrow-band emitted from the light distribution lens with respect to the optical axis of the observation window is narrower than the light distribution angle of the white light emitted from the light distribution lens.

9. The endoscope device according to claim 8, wherein a captured image under illumination by the first light output unit or a captured image under illumination by the second light output unit are alternately acquired and displayed side by side.

10. The endoscope according to claim 1, wherein the second light emitting element is positioned farther from the imaging unit in a transverse direction of the insertion tube than the first light emitting element, thereby causing the second illumination light to be incident on the single, annular light distribution lens over a wider range of directions than the first illumination light so that the single, annular light distribution lens transmits the second illumination light over a wider range of directions than the first illumination light.

11. The endoscope according to claim 1, wherein
the observation window is positioned at a forward end of the distal tip,
the single, annular light distribution lens has
an inner end adjacent to an outer end of the observation window,
an outer end adjacent a housing of the insertion tube,
a bending portion positioned between the inner and outer ends of the single, annular light distribution lens, and
the second light emitting element
is positioned in a transverse direction of the insertion tube farther from the inner end of the single, annular light distribution lens than the first light emitting element, so that
the first illumination light is incident on a spread portion of the single, annular light distribution lens, and
the second illumination light is incident on the single, annular light distribution lens over a wider range of directions than the first illumination light from the spread portion to the bending portion of the single, annular light distribution lens, thereby emitting second illumination light to pass through the single, annular light distribution lens at positions farther from the observation window in the longitudinal direction than the first illumination light from the first light emitting element, so that the single, annular light distribution lens transmits the second illumination light over a wider range of directions than the first illumination light.

12. The endoscope according to claim 1, wherein the single, annular light distribution lens has inner and outer ends, and a concave portion between the inner and outer ends, the inner end of the single, annular light distribution lens is adjacent to an outer end of the observation window, the second light emitting element is positioned in a transverse direction of the insertion tube farther from the inner end of the single, annular light distribution lens than the first light emitting element, and the single, annular light distribution lens transmits the second illumination light from the second light emitting element over a wider light distribution range than the first illumination light from the first light emitting element by the combined action of the concave portion of the single, annular light distribution lens and the positioning of the second light emitting element in the transverse direction of the insertion tube farther from the inner end of the single, annular light distribution lens than the first light emitting element.

13. The endoscope according to claim 1, wherein the single, annular light distribution lens transmits the first and second illumination light in different ranges of directions in response to different positionings of the first and second light emitting elements with respect to the imaging unit.

14. The endoscope according to claim 13, wherein the first light emitting element is closer to the imaging unit than the second light emitting element.

15. The endoscope device according to claim 8, wherein the single, annular light distribution lens transmits the first and second illumination light in different ranges of directions in response to different positioning of the first and second light emitting elements with respect to the imaging unit.

16. The endoscope device according to claim 15, wherein the first light emitting element is closer to the imaging unit than the second light emitting element.

17. The endoscope according to claim 1, wherein the single, annular light distribution lens has a concave portion, the second light emitting element is closer to the imaging unit than the first light emitting element, and the single, annular light distribution lens transmits the first and second illumination light in different ranges of directions in response to the different positionings of the first and second light emitting elements with respect to the imaging unit and the providing of the concave portion for the single, annular light distribution lens, resulting in the first illumination light from the first light emitting element being incident on the concave portion of the single, annular light distribution lens, thereby causing the first illumination light to be transmitted by the single, annular light distribution lens only in the first range of directions, and the second illumination light from the second light emitting element being incident on a portion of the single, annular light distribution lens spaced from the concave portion thereof, thereby causing the second illumination light to be transmitted by the single, annular light distribution lens only in the second range of directions.

18. The endoscope device according to claim 8, wherein the single, annular light distribution lens has a concave portion, the second light emitting element is closer to the imaging unit than the first light emitting element, and the single, annular light distribution lens transmits the first and second illumination light in different ranges of directions in response to the different positionings of the first and second light emitting elements with respect to the imaging unit and the providing of the concave portion for the single, annular light distribution lens, resulting in the first illumination light from the first light emitting element being incident on the concave portion of the single, annular light distribution lens, thereby causing the first illumination light to be transmitted by the single, annular light distribution lens only in the first range of directions, and the second illumination light from the second light emitting element being incident on a portion of the single, annular light distribution lens spaced from the concave portion thereof, thereby causing the second illumination light to be transmitted by the single, annular light distribution lens only in the second range of directions.

* * * * *